United States Patent
Basheer et al.

(10) Patent No.: US 7,034,168 B2
(45) Date of Patent: Apr. 25, 2006

(54) PROCESS FOR THE PRODUCTION OF PHOSPHOLIPIDS

(75) Inventors: Sobhi Basheer, Sakhnin (IL); Rassan Zuabi, Neen Village (IL); Avidor Shulman, Kiryat Tivon (IL); Neta Scheinman, Nesher (IL)

(73) Assignee: Enzymotec Ltd., Migdal HaEmek (IL)

( * ) Notice: Subject to any disclaimer, the term of this patent is extended or adjusted under 35 U.S.C. 154(b) by 80 days.

(21) Appl. No.: 10/700,320

(22) Filed: Nov. 3, 2003

(65) Prior Publication Data

US 2004/0171126 A1 Sep. 2, 2004

(51) Int. Cl.
*C07F 9/02* (2006.01)

(52) U.S. Cl. ............... 554/82; 554/79; 554/80

(58) Field of Classification Search ............. 554/82, 554/79, 80
See application file for complete search history.

(56) References Cited

U.S. PATENT DOCUMENTS

| | | | |
|---|---|---|---|
| 4,130,571 A | * | 12/1978 | Nakajima et al. ............ 554/82 |
| 5,538,874 A | | 7/1996 | Hattori et al. |
| 5,654,290 A | | 8/1997 | Bayon et al. |
| 6,268,187 B1 | | 7/2001 | Chung et al. |

FOREIGN PATENT DOCUMENTS

| | | |
|---|---|---|
| WO | WO 91/00918 | 1/1991 |
| WO | WO 99/15689 | 4/1999 |
| WO | WO 00/56869 | 9/2000 |

OTHER PUBLICATIONS

Virto Carmen et al, "Lysophosphatidylcholine synthesis with . . . lipase B (Novosym 435)" Enzime and Microbial Technology, vol. 26, No. 8, May 2000, pp. 630– 635, XP 002193135.
Pernas P. et al, "Phospholipid synthesis by . . . Solvents-"Biochemical and Biophysical Research Communications, vol. 168, No. 2, 1990, pp. 644–650, XP 002193136.
Maekawa N. et al: "Preparation of mixed . . . glycerophospholipids", XP 002231814 & JP 2000 281688 (Nippon Oil & Fats Co. Ltd. Japan), Oct. 10, 2000.
Plueckthun, A. et al: "Acyl and phosphoryl . . . specificity" Biochemistry (1982), 21(8), 1743–50, XP002231813.
Adlercreutz, P. et al, "Enzymatic conversions of polar lipids. Principles, problems and solutions", j. mOL cAT. b, eNZYMATIC 11, PP. 173–178 (2001).
Aura, A.M. et al, "Transesterification of Soy Lecithin by Lipase and Phospholipase", JAOCS, vol. 72, No. 11, pp. 1375–1378 (1995).
Svensoon, I., "Lipase–Catalyzed Transesterification of Phosphatidylcholine at Controlled Water Activity", JAOCS, vol. 69, No. 10, pp. 986–991 (1992).
Vitro et al., Enzyme & Microbial Tech., vol. 20, No. 8, May 200, pp. 630–635.*

* cited by examiner

*Primary Examiner*—Deborah D. Carr
(74) *Attorney, Agent, or Firm*—Martin Fleit; Paul D. Bianco; Fleit Kain Gibbons Gutman Bongini & Bianco

(57) ABSTRACT

A new enzymatic process for preparing 1,2-diacylated phospholipids using an enzyme preparation possessing phospholipase activity towards acylation at the sn-1 and sn-2 sites in a microaqueous reaction system. More particularly, the 1,2-diacyl-phospholipids produced according to the esterification/transesterification process are obtainable in high yield and purity and carry identical desired carboxylic acid, preferably fatty acid, acyl groups at the sn-1 and sn-2 positions. The process involves esterification/transesterification (acylation) of a glycerophospholipid, preferably glycerophosphoryl choline (GPC) with a desired carboxylic acid, preferably fatty acid, or their derivatives in the presence of the above mentioned appropriate enzyme preparation. The process of the invention further relates to a process for the production of 1-acyl-2-lyso-glycerophospholipid, preferably 2-lyso-PC by reacting glycerophospholipid, preferably glycerophosphoryl choline (GPC) with a desired carboxylic acid, preferably fatty acid, or their derivatives in the presence of a sn-1 specific phospholipase ($PLA_1$ or $PLA_{1,2}$) and a solvent, in a microaqueous medium.

37 Claims, 3 Drawing Sheets

PROCESS FOR THE PRODUCTION OF PHOSPHOLIPIDS

RELATED APPLICATION

This application is a continuation of International Application No. PCT/IL02/00344 filed May 2, 2002, the contents of which are here incorporated by reference in their entirety. Claim for priority under 35 USC 120 is hereby made.

BACKGROUND OF THE INVENTION

1. Field of the Invention

The present invention describes a new enzyme-catalyzed synthetic process for the production of 1-acyl-2-lyso and 1,2-di-acylated glycerophospholipids and their synthetic or natural analogues, wherein the acyl groups in the mono- and di-acyl compounds which may be the same or different each derived from a saturated or unsaturated, short-, medium- and long-chained linear or branched free carboxylic acid or a derivative thereof, preferably a free fatty acid or a derivative thereof, selected from the group consisting of fatty acid chloride, fatty acid alkyl ester, fatty acid vinyl ester, fatty acid anhydride and any other activated form of a fatty acid serving as a fatty acyl donor. In accordance with the present invention, there is provided an enzymatic esterification/transesterification (acylation) process for the production of 1,2-diacylated and 1-acylated-2-lyso phospholipids using as substrate glycerophosphorylcholine (GPC), or analogue derivative thereof, where the choline moiety can be substituted by ethanolamine, serine, inositol, glycerol or any other alcohol, together with a fatty acid derivative, as defined above. The reaction can be performed in a solvent or in a solvent-free microaqueous system, in the presence of a phospholipase which may be immobilized onto an insoluble matrix and is optionally surfactant coated (modified). The process of the present invention leads to the formation of 1-acyl-2-lyso-glycerophospholipids and 1,2-di-acylated glycerophospholipids, with a high conversion rate.

The present invention relates to the development of an enzymatic process for preparing 1-acylated- or 1,2-di-acylated phospholipids, and their synthetic or natural analogues. More specifically, it relates to a process for preparing 1,2-diacyl-3-glycerophospholipids and 2-lyso-3-glycerophospholipids of the formulae STR and STR1 respectively, wherein R and R' are the same or different and are each derived from a saturated or unsaturated, short-, medium- and long-chained linear or branched free carboxylic acid or derivative thereof, preferably a free fatty acid or derivative thereof, selected from the group consisting fatty acid chloride, fatty acid alkyl ester, fatty acid vinyl ester, fatty acid anhydride and any other activated form of a fatty acid serving as a fatty acyl donor. X in both formulae represents choline, serine, ethanolamine, glycerol, inositol, or any other appropriate alcohol moiety.

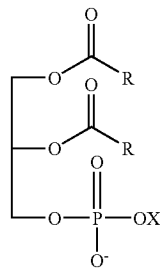

STR

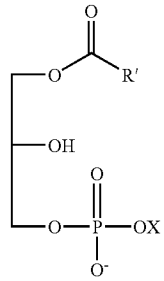

STR1

2. Prior Art

Phospholipids are the main structural components of the cell membrane. Soybeans and egg yolk are the major natural sources for obtaining phospholipids in commerce. This class of materials has been well recognized for their surface-active properties, therefore, phospholipids find extensive use in the food, cosmetics and pharmaceutical industries. The type of fatty acyl residues at the sn-1 and sn-2 positions (sites) in natural phospholipids vary, and their proportion in general depends on their source. For some practical applications it is favored to have phospholipids of defined structure with respect to the type of fatty acyl bound to the sn-1 or sn-2 positions of the glycerol skeleton. In some applications, other carboxylic acyl groups are needed, which may be derivatives of either fatty- or non-fatty acids. Phospholipids of defined structure are usually obtained from natural sources by fractionation or by means of liquid chromatography. Different chemical synthesis approaches have also been developed for the production of phospholipids with specific fatty acyl groups. The most widely practiced method for obtaining 1,2-diacylated phospholipids is based on a non-enzymatic reaction in which GPC or other glycerophospholipids react with an activated fatty acid derivative such as fatty acyl chloride or fatty acid anhydride. For example, dimyristoyl, di-stearoyl and di-oleoyl derivatives of phospholipids have been prepared with yields of 51.0%, 38.4% and 54.7%, respectively, by reacting cadmium chloride salt of GPC with the appropriate fatty acid chloride at room temperature for 3 hours (U.S. Pat. No. 4,130,571). When the reagents and the products of this reaction are in contact with each other for a prolonged time the percent of the formed by-products increased significantly. Furthermore, when using the fatty acyl chloride method, the preparation of phospholipids having highly unsaturated fatty acyl groups was not efficient for producing the desired products (U.S. Pat. No. 4,130,571). The chemical, non-enzymatic, synthesis route developed for the production of 1,2-diacylated phospholipids starting from GPC and fatty acid anhydride has shown improved results and less by-products (U.S. Pat. No. 4,130,571). For example, according to this method, di-palmitoyl derivative (yield: 90%), di-stearoyl derivative (yield: 81%) and di-oleoyl derivative (yield: 71%) were obtained by reacting cadmium chloride salt of GPC with the appropriate fatty acid anhydride and tetraethyl ammonium salt of the fatty acid. The preparation of polyunsaturated fatty acid derivatives in this process has encountered the production of high percentage of cyclic by-products, and consequently, the yield for the production of this type of phospholipids was relatively low (U.S. Pat. No. 4,130,571). In other words, the 1,2-diacyl yield is high when the fatty acid used as a substrate is saturated or monounsaturated, while it is low when the fatty acid is polyunsaturated.

Furthermore, the chemical synthesis of 1,2-diacyl-phospholipids, which utilizes a variety of acidic or basic reagents and environments, may harm the chiral center of natural phospholipids, a fact that is of crucial importance in pharmaceutical as well as in other applications.

A recent promising synthetic method to replace existing acyl groups in phospholipids with desired ones, has been developed based on using natural phospholipids as starting materials. Special enzymes have been used to perform this type of reaction in organic media. Many recent reports indicate (Adlercreutz P. et al., J. Mol. Cat B: Enzymatic 11, p. 173–178 (2001) and Aura A. M. et al. JAOCS, Vol 72, no. 11, p. 1375–1378 (1995)) that the fatty acyl moiety on the sn-1 and sn-2 positions in phospholipids can be replaced using different types of hydrolases, such as specific or non-specific lipases with broad substrate specificity and phospholipase $A_2$. Basically, many reports have shown that different lipases derived from various species are capable of incorporating specific fatty acids on the sn-1 position of phospholipids. For example, U.S. Pat. No. 6,268,187 describes an esterification process for preparing a lysophospholipid using lipase in the presence of glycerol-3-phosphate derivative, a fatty acid derivative and one or more salt hydrate pairs. Carmen Virto and Patrick Adlercreutz, Enzyme and Microbial Technology Vol. 26, 630–635 (2000), have demonstrated that immobilized lipase from *Candida antarctica* lipase B (Novozyme 435) was effective in the synthesis of lysophosphatidylcholine. The transesterification of glycerophosphorylcholine and vinyl laurate was carried out in a solvent-free system or in the presence of 50% (v/v) t-butanol. The lipase was selective for the sn-1 position of the glycerol backbone and almost no phosphatidylcholine was produced in the first 24 hours of the reaction. However, and probably due to acyl migration, the formation of phosphatidylcholine increased slowly if the reaction was incubated over a long period of time. Incorporation of a specific fatty acid on the sn-2 position using phospholipase $A_2$, was demonstrated. However, so far no practical and efficient method has been reported. Pernas, T. et al., Biochemical and Biophysical Research Communications, Vol. 168(2), 644–650 (1990), demonstrated that extracellular phospholipase $A_2$ can catalyze the esterification of lysophosphatidylcholine with oleic acid. Up to 6.5% of lysophosphatidylcholine can be esterified into phosphatidylcholine.

WO 91/00918 teaches a method for the preparation of a phospholipid with a carboxylic acid residue in the 2-position wherein a lysophospholipid is esterified with a corresponding carboxylic acid in the presence of the catalyst phospholipase $A_2$, the esterification taking place in a microemulsion with a water content of 0.1–2% by weight. According to this publication a 1,2-diacyl-glycerophospholipid (for example, 1,2-diacyl-PC) is formed from 2-lyso-glycerophospholipid (2-lyso-PC) in the presence of a carboxylic acid and phospholipase $A_2$. The reported yields of obtained 1,2-diacylated-phospholipids are in the range of 7–12%.

It seems that the highest yield for obtaining phospholipids having the desired acyl group on the sn-2 position using phospholipase $A_2$ for catalyzing the interesterification of 1,2-diacylphospholipid and a specific, desired fatty acid derivative, was reported to reach only the range of 6–7% (Svensson, I. JAOCS, Vol 69, No. 10, p. 986–991 (1992)). These reactions have basically been performed in a microaqueous organic medium or in a bi-phase reaction medium. The main disadvantage of using these methods for the production of tailor-made phospholipids is the competing hydrolysis reaction at the sn-2 site to yield 1-acyl-2-lyso-phosphatidyl choline as a by-product, which significantly reduces the recovery of the desired 1,2-diacyl-phospholipids. In addition, the degree of incorporation of a specific fatty acid at a desired position on the glycerol backbone of the phospholipid, using different combinations of enzymes, is generally low, and in most cases did not exceed 20% (Aura A. M. et al. JAOCS, Vol 72, no. 11, p. 1375–1378 (1995)). Although many lipases and phospholipases derived from various sources of microorganisms appear in the literature as involved in phospholipid modification, none of these enzyme preparations has been found to catalyze the production of 1,2-diacylated phospholipids having a desired structure in high yields.

An alternative method has recently been developed for the production of phospholipids with desired fatty acids on the sn-1 and sn-2 positions (U.S. Pat. No. 5,654,290). This method is based on a two-step enzymatic-chemical method wherein the first step constitutes the production of 2-lyso-phosphatidylcholine starting from glycerophosphorylcholine (GPC), a defined fatty acid derivative and an appropriate enzyme in microaqueous system. Lipases, such as Rhizomucor miehei lipase and Novozym 435 (Virto et al., Enzyme and Microbial. Technol., 26, p. 630–635, 2000)) are in general capable of catalyzing this type of reaction and to give relatively high yields of the product. The second step of the reaction is carried out by mixing the purified 1-defined acyl-2-lyso-phosphatidylcholine with an activated fatty acyl donor, such as fatty acid anhydride or fatty acyl chloride, in an organic solvent in the presence of a chemical catalyst to obtain the appropriate 1,2-diacyl-phosphatidylcholine. The enzymatic synthesis of lysophosphatidylcholine with lipases has been demonstrated in microaqueous organic media using GPC and different fatty acid derivatives as starting materials (Virto et al., Enzyme and Microbial. Technol. 26, p. 630–635 (2000)). Conversions of 70–88% of GPC to yield 1-acyl-2-lyso-phosphatid choline were achieved with different fatty acid derivatives, whereas up to 12% of 1,2-diacyl-phosphatidylcholine was formed as a by-product in the reaction. In most of these studies, the enzyme lipase B of *Candida antarctica* (Novozym 435) has been used for specific acylation at the sn-1 position of the glycerophospholipid and to produce the 1-acylated phospholipids. Due to migration of the 1-acyl group to the sn-2 position a consecutive interesterification reaction on the sn-1 hydroxyl group leads to the formation of 1,2-diacylphospholipids as a by-product (Virto et al., Enzyme and Microbial. Technol. 26, p. 630–635 (2000)). The obtained results in these reported studies showed that the lipase was very selective for the sn-1 position and the formation of 1,2-diacyl-phospholipids was not detected during the first hours of the reaction. Furthermore, only after most of the substrate GPC was consumed, the slow formation of 1,2-acyl-phosphatidylcholine was observed. In these studies, 1,2-diacyl-phosphatidylcholine was most likely formed by the migration of the acyl from the sn-1 position to the sn-2 position. It was indicated that high yields of 2-lysophosphatidylcholine were achieved in short time when vinyl ester of fatty acid or fatty acid anhydrides were used due to the favorable thermodynamic equilibrium. Furthermore, a high excess of fatty acid vinyl ester to GPC is necessary to achieve significant conversions.

Neither of the above discussed publications has demonstrated an enzymatic esterification/transesterification process for preparing a substantial yield of 1,2-diacyl-glycerophospholipid nor they demonstrated an esterification/transesterification process, using phospholipase $A_1$, for preparing 2-lyso glycerophospholipid from glycerophospholipid.

The preparation of 1,2-diacylated phospholipids in a highly efficient one-step process which should provide substantial economic benefits. Consequently, it is an object of the present invention to provide an efficient, enzymatic process for preparing 1,2-pre-determined, identical diacyl-phospholipid, preferably 1,2-diacyl-PC comprising the use of an enzyme preparation, referred to as $PLA_{1,2}$, in microaqueous reaction systems. It is yet a further object of the present invention to provide the said 1,2-pre-determined identical diacyl-phospholipid in a one-step enzymatic process. It is yet an additional object of the present invention to use the said $PLA_{1,2}$ enzyme preparation or a phospholipase enzyme that catalyzes acylation at the sn-1 position (site), referred to as $PLA_1$, for converting glycerophospholipid, preferably GPC, into 1-acyl-2-lyso-glycerophospholipid, preferably 1-acyl-2-lyso-PC.

SUMMARY OF THE INVENTION

The present invention provides a new enzymatic process for preparing 1,2-diacylated phospholipids comprising the use of an enzyme preparation possessing phospholipase activity towards acylation at the sn-1 and sn-2 sites in a microaqueous reaction system. More particularly, the 1,2-diacyl-phospholipids produced according to the esterification/transesterification process of the present invention are obtainable in high yield and purity and carry identical desired fatty acyl groups at the sn-1 and sn-2 positions. The process involves acylation of a glycerophospholipid, preferably glycerophosphoryl choline (GPC) with a desired carboxylic acid acyl donor, preferably fatty acid derivative in the presence of the above mentioned appropriate enzyme preparation. The process of the invention further relates to a process for the production of 1-acyl-2-lyso-glycerophospholipid, preferably 2-lyso-PC by reacting glycerophospholipid, preferably glycerophosphoryl choline (GPC) with a desired fatty acid derivative in the presence of a sn-1 specific phospholipase ($PLA_1$ or $PLA_{1,2}$).

BRIEF DESCRIPTION OF THE FIGURES

The invention will be described in more detail in conjunction with the drawing in which.

DETAILED DESCRIPTION OF THE INVENTION OF PREFERRED EMBODIMENTS

Figure 1:
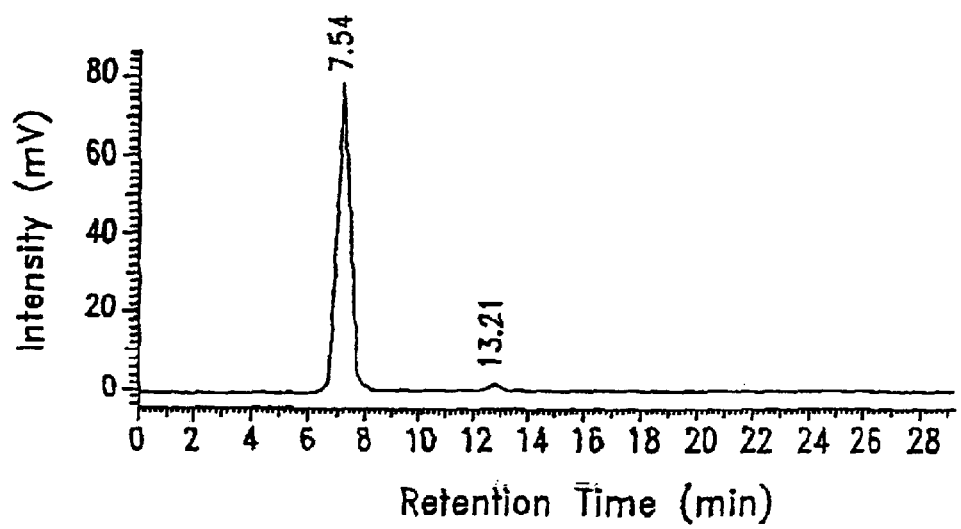
FIG. 1 illustrates an HPLC chromatogram of pure 1,2-dimyristioyl PC with Peak 1 representing 1,2-dimyristioyl PC and Peak 2 representing 1-myristioyl-2-lyso PC.

A major embodiment of the present invention is based on the surprising and unexpected finding that a commercial phospholipases $A_1$ product (Lecitase), provided by Sankyo (Japan), which is known to catalyze hydrolysis of the acyl group at the sn-1 position of mono- or di-acylated phospholipids, exhibits, under certain conditions, acylation activity at both the sn-1 and sn-2 sites of glycerophospholipids. This unexpected enzyme activity is substantially facilitated by immobilizing the enzyme onto an insoluble matrix and/or by coating the same with a surfactant material. This acylation activity at the sn-1 and sn-2 positions (sites) could not be demonstrated by any other tested commercial lipase or phospholipase $A_1$ enzymes, such as Novozymes (435 and 525) or Lecitase (Novo).

A phospholipase enzyme that demonstrates acylation activity at the sn-1 and sn-2 sites, is referred to herein as phospholipase $A_1, A_2$ (or shortly $PLA_{1,2}$).

Consequently, the said $PLA_{1,2}$ catalyzes the following new processes:
(a) reacting 1 mole GPC (or its analogue)+2 mole of a pre-determined fatty acid (or its derivative), in the presence of $PLA_{1,2}$, provides a high yield of 1,2-di-identical acyl-PC (or its corresponding analogue). It should be mentioned that the reaction requires an excess of fatty acid (or its derivative).
(b) reacting 1 mole of a GPC (or its analogue)+1 mole of a pre-determined fatty acid (or its derivative), in the presence of $PLA_{1,2}$ and a solvent (such as tert.-butanol), provides 1-desired acyl-2-lyso-PC (or its corresponding analogue). It should be mentioned that an excess of acid (or its derivative) is preferable.

The term "analogue" of GPC as used herein includes, but is not limited to, glycerophospholipids in which the choline moiety is replaced by ethanolamine, serine, inositol, glycerol or any other appropriate alcohol.

The term "fatty acids" (or their derivatives) as used herein includes a saturated or unsaturated, short-, medium- and long-chained linear- or branched fatty acid derivative, selected from the group consisting of free fatty acid, fatty acid chloride, fatty acid alkyl ester, fatty acid vinyl ester, fatty acid anhydride or any other activated form of a fatty acid serving as a fatty acyl donor. As is mentioned above, the fatty acid is included in the broader term of carboxylic acid and derivatives thereof.

The term "pre-determined" relates to a particular desired acyl group that is already linked, or is to be linked, at either of the sn-1 or sn-1 and sn-2 sites of the glycerol moiety.

These new processes, catalyzed by the $PLA_{1,2}$ enzyme preparation are further substantially facilitated using an enzyme immobilized on an insoluble matrix, optionally surfactant-coated.

According to the present invention, the starting material GPC (representing the above defined glycerophospholipids) or salt thereof, reacts with a pre-determined acylating agent selected from carboxylic acids or derivatives thereof, and preferably selected from fatty acid derivatives comprising free fatty acid, fatty acyl chloride, fatty acid alkyl ester, fatty acid vinyl ester, fatty acid anhydride and any other activated form of a fatty acid serving as a fatty acyl donor, in the presence of the enzyme $PLA_{1,2}$, to provide 1,2-desired, pre-determined diacyl-PC. According to another aspect of the present invention the same $PLA_{1,2}$ enzyme preparation can catalyze the esterification at the sn-1 position of GPC (or analogue thereof) in an organic solvent and microaqueous environment with a desired fatty acid derivative to provide 1-desired acyl-2-lyso-PC (or analogue thereof). According to another aspect of the present invention, it was found that a phospholipase $A_1$ enzyme preparation is capable of catalyzing the esterification/interesterification (acylation) at the sn-1 position of GPC (or analogue thereof) in an organic solvent and microaqueous environment with a desired fatty acid derivative to yield 1-desired acyl-2-lyso-PC (or analogue thereof).

The PLA$_{1,2}$ enzyme of the present invention used for the preparation of 1,2-desired diacyl-PC or 1-desired acyl-2-lyso PC (and analogue thereof) is optionally surfactant-coated (also referred to herein as modified), preferably with sugar fatty acid esters and may be immobilized by adsorption onto powdery matrices (such as silica, Celite, alumina), ion-exchange resins, or covalently bound to activated insoluble matrices as described in WO 00/56869 fully incorporated herein as a reference.

The starting material GPC (or analogues thereof can be used in the form of the free glycerophospholipid or its salt, for example, cadmium salt or barium chloride salt. These salts are usually considered as complex salts. The alcohol moiety bound to the phosphate group can be choline, ethanolamine, serine, inositol, glycerol or any other appropriate alcohol.

The phospholipase used in the process of the present invention (PLA$_{1,2}$) or an analogous enzyme that catalyzes acylation at both sn-1 and sn-2 sites may be usually obtained from microorganisms, in particularly, from species of the fungus *Aspergillus*, which is described in the U.S. Pat. No. 5,538,874. The choice of species or strain of fungus belonging to the genus *Aspergillus* (or any other microorganism genus) is not essential to the present invention, as long as the microorganism chosen produces the desired enzyme capable of catalyzing the processes of the present invention, yielding 1,2-diacylated glycerophospholipids. *Aspergillus oryzae*, for example, is defined under strain SANK 11870 or the strain available from the Institute of Fermentation (IFO) No. 30102, or the same strain available under ATCC No. 9642. Other tested phospholipases or lipases, for example the ones listed in Table 1, are not capable of efficiently catalyzing the production of 1,2-diacylated-glycerophospholipids.

TABLE 1

| Commercial name | Source | Manufacturer |
| --- | --- | --- |
| Lecitase Novo | | Novo Nordisk, DK |
| Novozyme 525 | *Candida Antarctica* B. sp. | Novo Nordisk, DK |
| Novozyme 435 | *Candida Antarctica* B. sp. | Novo Nordisk, DK |

A preferred embodiment of the present invention relates to a surfactant-coated enzyme complex immobilized on an organic or inorganic insoluble matrix which can be used to catalyze mono- and di-acylation of glycerophospholipids.

The enzymes involved in the processes of the present invention, namely PLA$_{1,2}$ and PLA$_1$ and lipases may be non-immobilized and surfactant-coated or preferably immobilized and optionally surfactant-coated. The immobilization of said enzymes onto insoluble matrices may be performed by three different methods as described in WO 00/56869: (i) immobilization through (physical) adsorption on inorganic or organic insoluble matrices; (ii) immobilization through ionic interactions on various ion exchange resins (polar or non-polar matrices); and (iii) immobilization through covalent immobilization to insoluble matrix, such as Eupergit® (organic matrix).

There are indications that coating phospholipases and lipases with a lipid surfactant, such as, but not limited to, fatty acid sugar ester types, enhances the catalytic activity of both enzymes and in most cases such a modification process renders slightly active crude enzyme to a highly active biocatalyst (WO 00/56869). Surfactant-coated (phospho) lipases immobilized on organic or inorganic matrices, are used for obtaining enzymatic interesterification/esterification reactions from which the (phospho)lipase enzyme can be easily recovered, recycled or used continuously.

In a preferred embodiment of the present invention the insoluble matrix is an inorganic insoluble matrix. The term "insoluble" refers to lack of solubility in both polar (e.g., water) and non-polar (hydrophobic) solvents. Preferably, the inorganic insoluble matrix is selected from the group consisting of alumina, aluminum stearate, Celite, calcium carbonate, silica gel, charcoal, calcium sulfate and ion-exchange resin, such as, Duolite A 568® and Amberlyst A21®.

Suitable organic solid matrices according to the present invention include Eupergit® C (C 250L) for covalent immobilization or any other organic solid matrix containing active group (or groups that may be activated) capable of covalently binding the enzyme. In another preferred embodiment of the present invention the enzyme represents 0.1–20, preferably 1–20 weight percent of the surfactant-coated enzyme complex. In yet another preferred embodiment of the present invention the enzyme represents 0.01–20 and preferably 0.5–5 weight percent of the surfactant-coated immobilized enzyme preparation. Preferably, the enzyme represents about 0.7 weight percent of the preparation.

According to a further preferred embodiment of the invention the employed surfactant is a lipid, which includes a fatty acid conjugated to a hydrophilic moiety. The fatty acyl is preferably monolaurate, monomyristate, monopalmitate, monostearate, dilaurate, dimyristate, dipalmitate, distearate, trilaurate, trimyristate, tripalmitate or tristearate. The hydrophilic moiety is preferably a sugar, such as, but not limited to, sorbitol, sucrose, glucose and lactose, glycerol or polyglycerol, a phosphate group, a carboxylic group or a polyhydroxylated organic residue. Typically, the fatty acid and the hydrophilic moiety are conjugated via ester or ether bonds.

The organic solvent is typically a hydrophobic solvent, such as, but not limited to, tert.-butanol.

For producing the insoluble matrix-immobilized surfactant-coated enzyme complex, the process described in WO 00/56869. The method includes the following steps: (a) an enzyme, an insoluble matrix and optionally a surfactant, are contacted in an aqueous solution, preferably a buffered solution; (b) conditions (e.g., sonication) are provided for the formation of the matrix-immobilized (surfactant-coated) enzyme complex. Two alternative schemes are available in this respect. In the first scheme the enzyme is first interacted with the surfactant and only thereafter the surfactant-coated enzyme is interacted with the matrix. In the second scheme, the enzyme is first interacted with the matrix and only thereafter the matrix-immobilized enzyme is interacted with the surfactant.

The method further includes the step of separating the matrix-immobilized (surfactant-coated) enzyme complex from the aqueous solution.

The method further includes the step of drying the matrix-immobilized (surfactant-coated) enzyme complex. Drying is preferably by freeze drying, fluidization or in an oven. Following drying, the matrix-immobilized (surfactant-coated) enzyme complex has between 0.1–45 and preferably 0.5–10 w/w % water.

In a preferred modification of said method, contacting the enzyme insoluble matrix and the surfactant within the aqueous solution is effected by dissolving the surfactant in an organic solvent (e.g., ethanol) for obtaining a dissolved surfactant solution, mixing the enzyme and the dissolved surfactant solution (e.g., dropwise) in the aqueous solution, sonicating the resulting suspension, and adding the insoluble matrix into the aqueous solution. Alternatively, the enzyme is first interacted with the insoluble matrix and only thereafter with the surfactant.

Water is added into the reaction system preferably in the range of less than 30% volume of the reaction medium. The diacylation reaction is best performed in a solvent-free environment, where the carboxylic acyl donor serves also as a solvent. In such case, the water content is less than 5%, preferably 0.5–3%. There is also water in the enzyme preparation, but probably not accessible being tightly adsorbed in the matrix. In the case of monoacylation reaction in addition to organic solvent there are less than 5% water, preferably 0.5–3%.

According to a preferred embodiment, the matrix-immobilized surfactant-coated enzyme complex represents 1–30 weight percent of the reactants. In a yet another preferred embodiment, the glycerophospholipid substrate is suspended in the same organic solvent or in the medium constituted of the fatty acid derivative in the presence of water in the range of less than 30% volume of the reaction medium.

Reference is now made to the following examples, which together with the above description illustrate the invention in a non-limiting manner.

EXAMPLES

Experimental Procedures

A. Materials

Different crude lipase and phospholipase preparations were tested in this study. Table 1 lists commercially available phospholipase and lipase preparations that were employed in this study, as well as their species source and supplier. All fatty acid derivatives employed in this study were obtained from Fluka (Switzerland) and Sigma-Aldrich (80% to 99% pure). Buffer salts and the inorganic matrices used as supports for the surfactant-coated lipase complexes, including Celite, alumina and silica, were obtained from Sigma (USA), and the ion-exchange resins and other enzyme adsorbents were the products of Rohm and Haas (Belgium).

Analytical grade n-hexane, tert.-butyl alcohol and other solvents employed were from Bio Lab (Israel). Sorbitan fatty acid esters including sorbitan monolaurate, sorbitan monomyristate, sorbitan monopalmitate and sorbitan monostearate and sucrose fatty acid esters including mixtures of mono-, di- and tri-stearate sucrose esters of variable HLB values were obtained from Kao Pure Chemicals Ind. (Tokyo, Japan).

B. Methods

1. Enzyme Modification and Immobilization Through Adsorption (Mainly onto Insoluble Supports Crude enzyme was first coated with a lipid-surfactant material. A typical enzyme modification and immobilization procedure was as follows: crude enzyme (2 g) (protein content approximately 70 mg/100 ml), was dissolved in 100 ml phosphate or tris buffer solution with an appropriate pH, and magnetically stirred at 10° C. for 30 min. 100 mg lipid-surfactant (or other enzyme modifier) dissolved in 0.5 ml ethanol (or other solvents) were added dropwise into the stirred solution. The resulting enzyme solution was sonicated for 15 min and then vigorously stirred at 10° C. for 3 hours. 2 g insoluble organic matrix (such as polypropylene, aluminum stearate) or 2 g inorganic matrix (such as Celite, alumina, silica gel or other ceramic supports) were added into the stirred enzyme solution. The solution was magnetically stirred for a further 5 hours at 10° C. The precipitate was collected by centrifugation at 12000×rpm (Sorval Centrifuge, model RC-5B) or by filtration, and then was lyophilized.

For preparing a non-modified immobilized enzyme complex, the above procedure was applied, however, without adding the modifying reagent (sugar fatty acid ester). Alternatively, commercially immobilized enzymes (for example, Novozyme 435 by Novo) are applicable as well with or without modification (surfactant coating) procedure.

2. Enzyme Modification and Immobilization Through Ionic Adsorption

The above-described modification and immobilization procedures were further applicable in conjunction with immobilization onto ion-exchange resins. The types of resin used include: weak to strong basic anion exchange resins, weak to strong acidic cationic exchange resins and non-polar to weak-polar ion-exchange resins. Examples of commercially available resins that may be used: Dowex® 22, Dowex® 1x2-400, Dowex®, 2x8-100, cellulose phosphate, Amberlite® IRA-95, Amberlite® IRA-200, Amberlite® IRA-900, Amberlite® XAD-7, Amberlite® XAD-16, Diannon® SA-10A, Ectoela® cellulose, Sephadex® and sulfoxyethylcellulose (all were obtained from Sigma, USA), Duolite® A 568 and Amberlyst® A21 (Rohm and Haas-Belgium).

A typical modified-immobilized enzyme is prepared according to the aforementioned procedure, however after sonication, an ion exchange resin (1–20 g) is added into the stirred enzyme solution.

For preparing a non-modified immobilized (using ion exchange resin) enzyme complex, the above procedure is applied, however, without adding the modifying reagent (sugar fatty acid ester).

3. Enzyme Modification and Immobilization Through Covalent Binding

In principle two different immobilization procedures may be applied. According to the first procedure, the enzyme is primarily coated with a surfactant and then the surfactant-coated enzyme complex is covalently bound to an activated matrix, such as, for example, Eupergit, which contains active oxirane groups. It should be pointed out that any other activated matrix that contains an active group capable of covalently coupling to the surface amino groups, or any other functional group of the enzymes, should be applicable. To this end, 1 g crude enzyme (containing 1–20% weight protein) is dissolved in 100 ml phosphate buffer, pH 5.8. The enzyme solution is vigorously stirred with a magnetic stirrer at 10° C. for 30 minutes. 100 mg sorbitan mono-stearate, dissolved in 0.5 ml ethanol, are added dropwise to the stirred enzyme solution. The resulting colloidal enzyme solution is sonicated for 10 minutes and then stirred for 3 hours at 10° C. 20–5 g Eupergit® C or Eupergit® C 250L and optionally, 0.5 ml solution of 5% hydrogen peroxide are added to the enzyme solution and the resulting suspension is gently handshaken for 1 minute, and then incubated for 48 hours at 23° C. The precipitate is filtered, washed with phosphate buffer, pH 5.8, and is freeze-dried overnight.

According to the second procedure, the enzyme is first bound to the Eupergit matrix and then the covalently-bound enzyme may be coated with a surfactant—as follows:

1 g crude enzyme is dissolved in 100 ml phosphate buffer, pH 5.8. The enzyme solution is vigorously stirred with a magnetic stirrer at 10° C. for 30 minutes. 1–5 g Eupergit® C or Eupergit® C 250L and optionally 0.5 ml solution of 5% hydrogen peroxide are added to the enzyme solution and the resulting suspension is gently handshaken for 1 minute and then incubated for 48 hours at 23° C. 100 mg sorbitan mono-stearate dissolved in 0.5 ml ml ethanol are added dropwise to the suspension under a gentle shake. The resulting suspension is sonicated for 10 minutes and incubated at 10° C. for 6 hours. The precipitate is filtered, washed with phosphate buffer, pH 5.8, and then freeze-dried overnight.

Protein determinations, according to the Bradford method, indicated that enzyme preparations prepared according to this method may contain 0.1–10 wt % protein.

4. Acylation Reaction Conditions

The acylation reactions of glycerophospholipids with fatty acid derivatives were initiated by adding an enzyme preparation (100 mg) to a mixture of a glycerophospholipid and a fatty acid derivative dissolved or suspended in organic solvent. The acylation reaction was also carried out in a solvent-free system in which the fatty acid derivative served also as a reaction medium. The reaction medium was shaken at the temperature range of 20–80° C. Samples were periodically removed, diluted with 50%:50% of ethanol:water solution (or just ethanol), filtered with Millipore filters (0.45 µm) and then injected to an HPLC system. The yield of products, calculated as percent peak area ratio between 1,2-diacyl- and 2-lyso-products, or the conversion rate of glycerophospholipid substrate, was calculated by determining the concentration of the formed mono- and/or diacylated glycerophospholipids with time.

Example 1

Preparation of 1,2-diacylated Glycerophospholipids Containing Fatty Acyl Groups at the sn-1 and sn-2 Positions This example relates to the preparation of 1,2-diacyl-glycerophosphlipids, using different preparations of phospholipase $A_1$ (Lecitase, Sankyo, Japan), referred herein to as $PLA_{1,2}$, (or "the enzyme") in a solvent-free system.

(A). 50 mg enzyme preparation obtained from the genus *Aspergillus*, the strain SANK 11870 (or from other strains of the same micro-organism, as described in U.S. Pat. No. 5,538,874, Sankyo-Japan) were added to a mixture of 10 mg GPC, 5–10 µl water and 0.5 ml vinyl laurate. The reaction system was shaken at 60° C. Samples were withdrawn periodically, diluted appropriately, filtered and analyzed by HPLC.

Table 2 demonstrates the yield (in terms of percent area ratio) of the products obtained, 1-mono-lauroyl glycerophosphatidylcholine and 1,2-di-lauroyl glycerophosphatidylcholine, using different preparations of phospholipase $A_1$ (Lecitase, Sankyo), referred to as $PLA_{1,2}$, after 48 hours.

TABLE 2

The peak area ratio (%) of 1-mono-lauroyl-glycerophosphatidylcholine and 1,2-di-lauroyl-glycerophosphatidylcholine obtained after 48 h at 60° C., using different preparations of phospholipase $A_1$ (Lecitase, Sankyo), referred to as $PLA_{1,2}$, in a microaqueous medium. The surfactant is sorbitan monooleate (SMO).

| Enzyme preparation | 1-mono-lauroyl-2-lysophosphatidylcholine (%) | 1,2-di-lauroyl-phosphatidylcholine (%) |
|---|---|---|
| Crude Lecitase (Sankyo) | 42.9 | 57.1 |
| Immobilized on Duolite A 568 + SMO | 15.3 | 84.7 |
| (pH = 4.5); 5 µl water Immobilized on Duolite A 568 + SMO | 26.5 | 73.5 |
| (pH = 5.8); 5 µl water Immobilized on Duolite A 568 + SMO | 32 | 68 |
| (pH = 4.5); 10 µl water Immobilized on Duolite A 568 + SMO | 38.2 | 61.8 |
| (pH = 5.8); 10 µl water Immobilized on Duolite A 568 + SMO | 16 | 84 |
| (pH = 6.0); 5 µl water | | |

Table 2 demonstrates that coating Lecitase (Sankyo) with the sugar fatty acid ester, sorbitan monooleate and then adsorbing the modified enzyme on Duolite A 568, resulted in a substantial increment in the production of the 1,2-diacyl product. In such case, the production of 1,2-dilauroyl derivative is over 80% yield (calculated as percent peak area ratio between 1,2-diacy- and 2-lyso-products). It is assumed that increasing the time of the reaction over 48 hours should result in increasing the yield of 1,2-diacyl compounds even further. Similar results were obtained when the enzyme was first modified with SMO and then immobilized onto Duolite® A568. Table 2 further demonstrates some variations in the yields of 1-lauoroyl-2-lyso-PC and 1,2-lauroyl-PC in accordance with applied pH and the amount of water inserted into the reaction medium.

It should be pointed out that the crude enzyme catalyzes the 1,2-diacylation reaction with a conversion rate of GPC of less than 5%, whereas the same enzyme in a (modified) immobilized form catalyzes the reaction with a conversion rate of GPC higher than 40% and it may reach under optimal conditions the conversion rate of 90%.

(B). 8 g enzyme preparation described in (A) hereinabove were added to a mixture of 10.53 g GPC, 250 g vinyl myristate. Before inserting the enzyme complex, the mixture should be well stirred and at 60° C. Samples of 20 µl were withdrawn periodically, diluted appropriately (with 1 ml absolute ethanol), filtered and analyzed by HPLC. Highly purified 1,2-dimyristioyl-PC was obtained (DMPC), following employing further purification steps (FIG. 1). The product was analyzed by an $^1$H-NMR for verify its chemical identity. Similar results were obtained using vinyl palmitate and GPC as substrates.

(C) No substantial synthesis of 1,2-diacylated glycerophospholipids is obtained when using lipase such as Novozym 525 and Novozym 435 (derived from the species

*Candida antarctica* and *Candida antarctica* B, respectively; Novo Nordisk A/S, Denmark), as well as phospholipase $A_1$ lecitase (Novo). These enzymes, in contrast to the phospholipase $A_1$ ($PLA_{1,2}$) of Examples A and B above do not show 1,2 di-acylating activity, and consequently cannot be considered as enzymes having $PLA_{1,2}$ activity.

(i) 50 mg lipase (Novozym® 525) were added to a mixture of 10 mg GPC, 5–10 µl water and 1 ml vinyl laurate. The reaction system was shaken at 60° C. for 48 hours. Samples were withdrawn periodically, diluted appropriately, filtered and analyzed by HPLC.

Table 3 demonstrates the yield (in terms of percent area ratio) of the products obtained, 1-mono-lauroyl-glycerophosphatidylcholine and 1,2-di-lauroyl-glycerophosphatidylcholine, using different preparations of Novozym 525, after 48 hours in a microaqueous media.

TABLE 3

The products, 1-mono-lauroyl-glycerophosphatidylcholine and 1,2-di-lauroyl-glycerophosphatidylcholine, obtained using different preparations of Novozym® 525 after 48 hours in microaqueous system. The surfactant was SMO.

| Enzyme preparation Novozym® 525 | 1-lauroyl-2-lysophosphatidylcholine (%) | 1,2-di-lauroyl-phosphatidylcholine (%) |
|---|---|---|
| Crude Novozym® 525 | 79.0 | 21 |
| Immobilized on Duolite® 568 + SMO; 5 µl water | 94.2 | 5.8 |
| Immobilized on Duolite® 568 + SMO; 10 µl water | 97.2 | 2.8 |

Table 3 compares Novozym® 525 which possesses a relatively high acylation activity of GPC with the data obtained in Table 2, using Lecitase® ($PLA_{1,2}$). The results presented in Table 3 reveal that SMO modified-immobilized Novozym® 525 possesses selective catalytic activity towards monoacylation of GPC at the sn-1 position. The yield (in terms of percent area ratio) of formed 1-mono-lauroyl-glycerophosphatidylcholine reached over 94% while the maximum yield of 1,2-di-lauroyl-glycerophosphatidylcholine was less than 6% when SMO-modified Novozym® 525-immobilized onto Duolite® A568 was used.

It should be pointed out that the crude enzyme catalyzes the acylation reaction with a conversion rate of GPC of less than 5%, whereas the same enzyme in a (modified) immobilized form catalyzes the reaction with much higher conversion rates of GPC.

(ii) 50 mg commercially immobilized lipase (Novozym® 435) were added to a mixture of 10 mg GPC, 5–10 µl water and 1 ml vinyl laurate. The reaction system was shaken at 60° C. for 48 hours. Samples were withdrawn periodically, diluted appropriately, filtered and analyzed by HPLC.

Table 4 demonstrates the yield (in terms of percent area ratio) of the products obtained, 1-mono-lauroyl-glycerophosphatidylcholine and 1,2-di-lauroyl-glycerophosphatidylcholine, using Novozym 435, after 48 hours in a microaqueous media.

TABLE 4

The products 1-mono-lauroyl-glycerophosphatidylcholine and 1,2-di-lauroyl-glycerophosphatidylcholine, obtained using Novozym® 435 after 48 hours in microaqueous system. The surfactant was SMO.

| Novozym® 435 | 1-lauroyl-2-lysophosphatidylcholine (%) | 1,2-di-lauroyl-phosphatidylcholine (%) |
|---|---|---|
| Commercially immobilized; 5 µl water | 94.3 | 5.7 |
| Commercially immobilized; 10 µl water | 90.3 | 9.7 |

Table 4 compares Novozyme® 435 which possesses a relatively high acylation activity of GPC with the data obtained in Table 2, using Lecitase® ($PLA_{1,2}$). The results presented in Table 4 reveal that commercially immobilized Novozyme® 435 possesses selective catalytic activity towards mono-acylation of GPC at the sn-1 position. The yield (in terms of percent area ratio) of obtained 1-monoacylated-2-lyso-PC reached over 90% while the maximum yield of 1,2-diacylated-PC was less than 10%.

(iii) 50 mg phospholipase $A_1$ (Lecitase Novo) were added to a mixture of 10 mg GPC, 5–10 µl water and 1 ml vinyl laurate. The reaction system was shaken at 60° C. for 48 hours. Samples were withdrawn periodically, diluted appropriately, filtered and analyzed by HPLC.

Table 5 demonstrates the yield (in terms of percent area ratio) of the products obtained, 1-mono-lauroyl-glycerophosphatidylcholine and 1,2-di-lauroyl-glycerophosphatidylcholine, using different preparations of Lecitase Novo after 48 hours in a microaqueous media.

TABLE 5

The products 1-mono-lauroyl-glycerophosphatidylcholine and 1,2-di-lauroyl-glycerophosphatidylcholine, obtained using different preparations of Lecitase Novo after 48 hours in microaqueous system. The surfactant was SMO.

| Enzyme preparation Lecitase Novo | 1-lauroyl-2-lysophosphatidylcholine (%) | 1,2-di-lauroyl-phosphatidylcholine (%) |
|---|---|---|
| Crude Lecitase Novo | Negligible | Negligible |
| Immobilized on Duolite® 568 + SMO; 5 µl water | 86 | 14 |
| Immobilized on Duolite® 568 + SMO; 10 µl water | 94.7 | 5.3 |

Table 5 compares Lecitase Novo which possesses acylation activity of GPC with the data obtained in Table 2, using Lecitase® ($PLA_{1,2}$). The results presented in Table 5 reveal that SMO modified-immobilized Lecitase Novo possesses selective catalytic activity towards monoacylation of GPC at the sn-1 position. The yield (in terms of percent area ratio) of obtained 1-monoacylated-2-lyso-PC reached over 85% while the maximum yield of 1,2-diacylated-PC was less than 15%, when SMO-modified Lecitase (Novo)-immobilized onto Duolite® A568 was used. However, it well may be that the same enzyme under different conditions will also exhibit 1,2-diacyloation catalytic activity to a certain degree.

In contrast to Lecitase® of Sankyo ($PLA_{1,2}$) the data presented above reveals that immobilized lipase (Novozyme® 435 and 525) as well as immobilized phospholipase A$_1$ (Lecitase Novo) show a selective 1-monoacylation activity, whereas the conversion rate of GPC to 1,2-diacylated GPC remained relatively low in these cases (less than 15%).

Example 2

Preparation of 1-acylated-2-lyso-glycerophospholipids Using Lecitase® (Sankyo) Having PLA$_{1,2}$ Activity.

It was found that the same Lecitase of Sankyo (PLA$_{1,2}$) that in the absence of a solvent catalyzes the production of 1,2-diacyl-glycerophospholipids is capable, in the presence of an organic solvent, such as tert.-butanol, to catalyze the production of 1-acyl-2-lyso-glycerophosphlipids. Much less 1,2-diacylglycerophosphlipid is formed in the presence of tert.-butanol compared to the same reaction but when no solvent is present.

(A) The Preparation of Modified-immobilized Lecitase® (PLA$_{1,2}$; Referred to as "the Enzyme") Complex The enzyme was dissolved in a phosphate buffer (such as, for example, K$_2$HPO$_4$ and KH$_2$PO$_4$, pH=5). Duolite A568 (or Amberlite XAD 7) was washed with de-ionized water several times (3–7 times). The dissolved enzyme was added to the washed Duolite A568 (or Amberlite XAD 7) and the formed suspension was vigorously stirred for 4 hours. After 4 hours SMO, either non-treated or dissolved in EtOH, was added to the enzyme+Duolite (or Amberlite) suspension while stirring. The formed enzyme+Duolite (or Amberlite)+ SMO suspension was stirred for overnight, followed by filtration the suspension through 20 μm filter paper and washing the precipitate (cake) with phosphate buffer.

The filtration procedure is very quick, and foam is formed at the filtrate so big vessels are preferred. The filtration cake is the surfactant-coated (modified)-immobilized enzyme complex. The obtained immobilized enzyme complex was dried at room temperature using vacuum of 0.1 to 5 mbar and stored at −20° C.

(B) The Esterification Reaction Catalyzed by the Surfactant-coated (Modified)-immobilized Enzyme Complex as Prepared in (A) Above The vinyl stearate (or vinyl palmitate) was mixed with tert.-butanol. The surfactant-coated (modified)-immobilized enzyme complex prepared in (A) was added to the vinyl stearate (or vinyl palmitate) in tert.-butanol at 50–70° C., followed by the addition of GPC and mixing. Foam can be formed during the mixing. Acetaldehyde was released during the esterification/transesterification reaction.

Note: it is possible to add the reactants in a different order; for example, GPC may be added first to the reaction mixture. However, it was found that adding GPC last to the reaction mixture is preferable for reaching better mixing of the GPC in the reaction mixture.

The reaction was carried out at either 60° C. or 70° C. Furthermore, it was performed in a series of different volumes (such as, for example, 50 ml, 1, 20 and 100 liters).

The desired product from this reaction is 1-stearoyl-2-lyso-PC (or 1-palmitioyl-2-lyso-PC) with conversion level of 30–95%. 1,2-Distearoyl-PC or 1,2-dipalmitioyl-PC (between 0.1 and 10%) and free stearic (or palmitic) acid are by-products of the reaction. The crude product mixture is a white-yellow solid at room temperature and liquid at 40° C. The main component of the crude product mixture is non-reacted vinyl stearate (or vinyl palmitate) in addition to the desired product. The immobilized enzyme complex is removed from the reaction mixture and recycled.

Example 2.1

The reaction was performed in 1 l Jacketed reactor with a stirrer at 60° C., for 200 hours.

The reaction mixture contained:
0.0288 Kg GPC
0.45 Kg vinyl stearate (VS)
0.0225 Kg immobilized-modified enzyme complex
0.15 lit t-BuOH The VS was mixed with the t-BuOH to obtain a clear solution, the immobilized enzyme complex and the GPC were added when the solution was at 60° C.

The rate of conversion was 67%.

Figure 2:
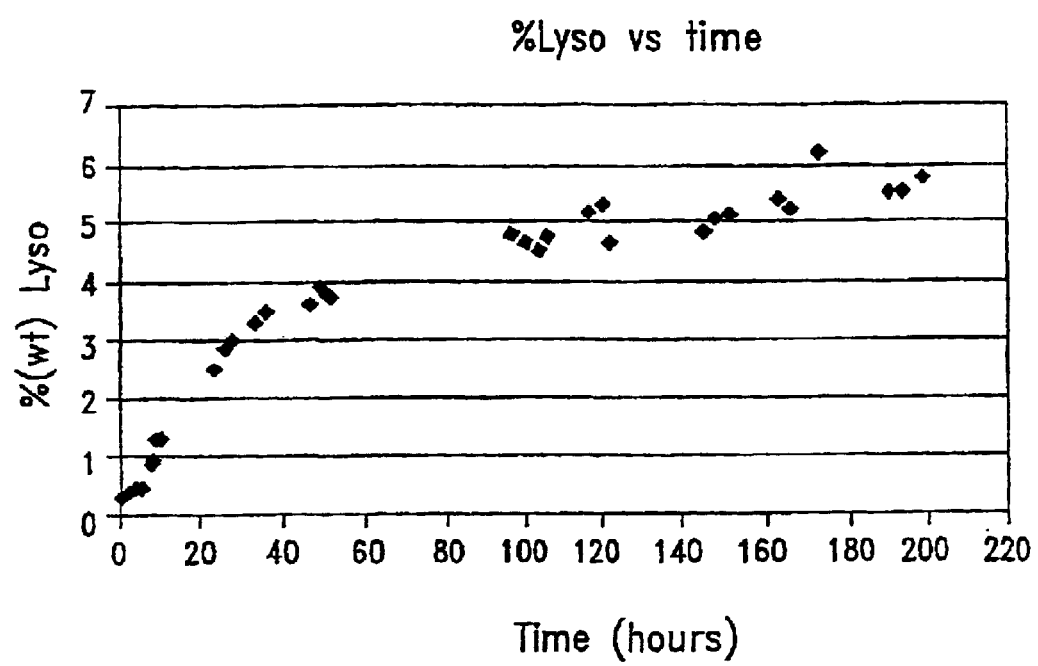
FIG. 2 illustrates a kinetic curve of 1-stearoyl-2-lysoPC production in 1 liter reaction volume.

The kinetic curve of the production of 1-stearoyl-2-lyso-PC is described in FIG. 2.

Example 2.2

The reaction was performed in 100 l Jacketed reactor with a stirrer at 60° C., for 120 hours. The reaction mixture contained:
4 Kg GPC
60 Kg VS
3 Kg immobilized-modified enzyme complex
20 lit t-BuOH The VS was mixed with the t-BuOH, the immobilized enzyme and the GPC were added when the solution was at 60° C.

The rate of conversion was 75% after 90 hours.

Figure 3:
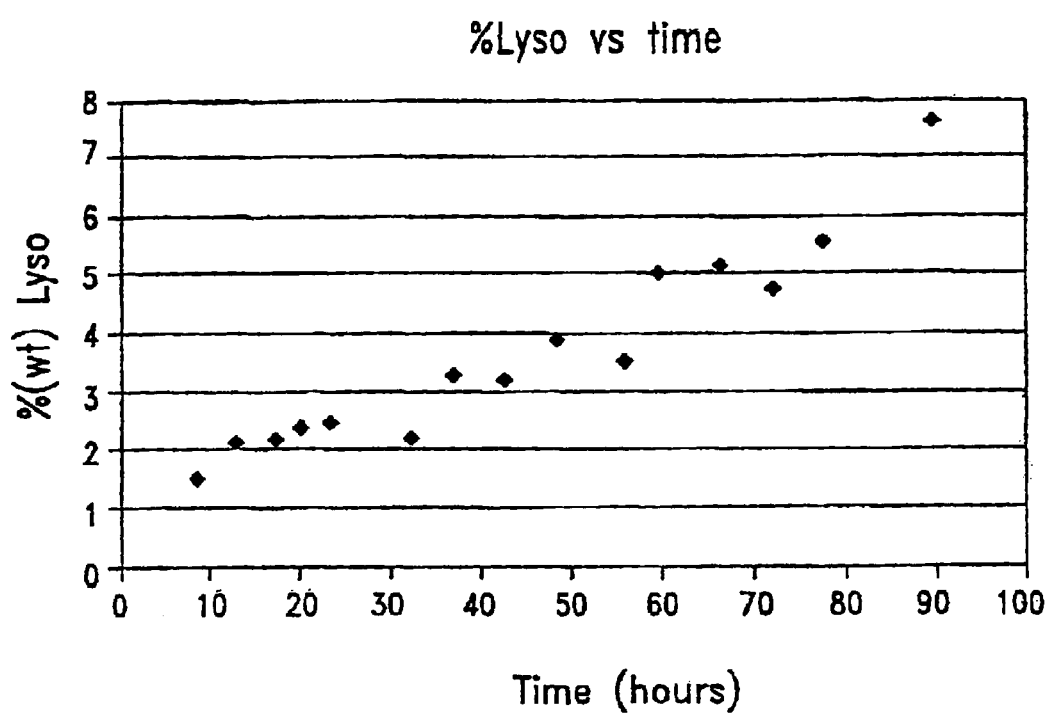
FIG. 3 illustrates a kinetic curve of 1-stearoyl-2-lysoPC production in 100 liter reaction volume.

The kinetic curve of the production of 1-stearoyl-2-lyso-PC is described in FIG. 3

Example 2.3

The reaction was performed in a 1 l Erlenmeyer in a shaker-incubator at 60° C., for 4 days. The reaction mixture contained:
0.025 Kg GPC
0.375 Kg VS
0.015 Kg immobilized-modified enzyme complex
0.1 lit t-BuOH The VS was mixed with the t-BuOH followed by addition of GPC and stirring the mixture for half an hour at 60° C. Then the 0.01 Kg of the immobilized enzyme complex was added. The mixture was stirred overnight and then another 0.005 Kg of immobilized enzyme complex added. The stirring was continued for 4 days.

The rate of conversion was 70%.

Example 2.4

The reaction was performed in a 0.25 l Erlenmeyer with a stirrer at 70° C., for 1 day. The reaction mixture contained:
0.0025 Kg GPC
0.0375 Kg VS
0.0019 Kg immobilized-modified enzyme complex
0.0125 lit t-BuOH The VS was melted with the t-BuOH, followed by addition of GPC and stirring the mixture for half an hour at 70° C. Then the immobilized enzyme complex was added.

The reaction mixture was stirred for 1 day.

The reaction conversion is in the same level as detailed above.

Example 2.5

The reaction was performed in a shaker-incubator at 60° C., for 3 days. In this reaction vinyl palmitate (VP) was reacted instead of vinyl stearate.

The obtained product is 1-palmitioyl-2-lyso-PC.

The reaction mixture contained:
0.005 Kg GPC
0.075 Kg VP
0.005 Kg immobilized-modified enzyme complex
0.025 lit t-BuOH The VP was mixed with the t-BuOH, followed by addition of GPC and stirring the mixture for half an hour at 60° C. Then the immobilized enzyme complex was added.

The reaction mixture was stirred for 3 days.

The reaction conversion is in the same level as detailed above.

Example 2.6

The reaction was performed in an Erlenmeyer in a shaker-incubator at 60° C. In this reaction Amberlite XAD 7 serves as insoluble matrix instead of Duolite A568. The reaction mixture contained:
0.0025 Kg GPC
0.0375 Kg VS
0.0019 Kg immobilized-modified enzyme complex
0.0125 lit t-BuOH The VS was mixed with the t-BuOH, followed by addition of GPC and stirring the mixture for half an hour at 60° C. Then the immobilized enzyme complex was added.

The reaction mixture was stirred for 25 hours.

The reaction conversion is in the same level as detailed above for the immobilized enzyme on Duolite A568.

Example 2.7

The reaction was performed in an Erlenmeyer in a shaker-incubator at 60° C. In this reaction recycled VS was used in the reaction instead of non-treated, fresh new VS.

The reaction mixture contained:
0.005 Kg GPC
0.075 Kg VS
0.005 Kg immobilized (Duolite A568)-modified enzyme complex
0.025 lit t-BuOH The VS was mixed with the t-BuOH, followed by addition of GPC and stirring the mixture for half an hour at 60° C. Then the immobilized enzyme complex was added.

The reaction mixture was stirred for 4 days.

At the end of the reaction the immobilized enzyme complex was separated from the reaction mixture. The remained tert.-butanol was removed from the reaction mixture by vacuum, followed by mixing the reaction mixture with an appropriate organic solvent under conditions in which VS is soluble whereas the product precipitates. Following removal of the solvent (using vacuum) the recovered VS was used for recycled esterification procedures.

Another three successive reactions were made using the same recycled VS. The rate of conversion remained constant in all three successive reactions and the conversions were in the same level as outlined above.

Example 3

The preparation of 1-acylated-2-lyso-glycerophospholipids using the enzyme phospholipase $A_1$ catalyzing esterification or acylation at the sn-1 position.

Another aspect of the present invention is the surprising finding that the hydrolyzing phospholipase $A_1$ is capable of catalyzing under certain conditions the esterification/transesterification (acylation) of the glycerophospholipids at the sn-1 position.

The reaction was performed using Lecitase Novo ($PLA_1$) as described in Example 1 (iii). The obtained data is summarized in Table 5. The results presented in Table 5 reveal that SMO modified-immobilized Lecitase Novo possesses selective catalytic activity towards mono-acylation of GPC at the sn-1 position. The yield (in terms of percent area ratio) of obtained 1-monoacylated-2-lyso-PC reached over 85% while the maximum yield of 1,2-diacylated-PC was less than 15%, when SMO-modified Lecitase (Novo)-immobilized onto Duolite® A568 was used.

Other phospholipases $A_1$ that catalyze the hydrolysis of the acyl group at sn-1 position may be as well capable of catalyzing esterification/transesterification (acylation) at sn-1 position, under the conditions described above, and consequently, they are included within the scope of the present invention. Furthermore, various matrices for immobilization of the (modified) enzyme, such as, Duolite XAD 761, Duolite A7HP and many others are applicable according to the present invention.

It is to be understood that the invention is not limited in its application to the details of construction and the arrangement of the components set forth in the above description. The invention is capable of other embodiments or of being practiced or carried out in various ways. Also, it is to be understood that the phraseology and terminology employed herein is for the purpose of description and should not be regarded as limiting.

What is claimed is:

1. A process for the production of 1,2-diacylated-glyceropospholipids and their synthetic or natural analogues, wherein the 1-acyl and 2-acyl groups are predetermined and identical, comprising contacting in a microaqueous environment a glycerophospholipid with a carboxylic acid acyl donor in the presence of a phospholipase enzyme capable of catalyzing an esterification/transesterification/acylation at both the sn-1 and sn-2 positions of said gylcerophospholipid.

2. A process according to claim 1, wherein the water content in the reaction mixture is less than 30% by volume of the volume of the reaction mixture, preferably less than 5%, more preferably 0.5–3%.

3. A process according to claim 1, wherein said glycerophospholipid is selected from the group consisting of glycerophosphoryl choline (GPC) and derivatives thereof, In which derivatives the choline moiety is replaced by ethanolamine, serine or an alcohol, preferably inositol or glycerol.

4. A process according to claim 1, wherein said carboxylic acid acyl donor is a fatty acid acyl donor.

5. A process according to claim 4, wherein said fatty acid acyl donor is a saturated or unsaturated, short-, medium- or long-chained linear or branched fatty acid derivative.

6. A process according to claim 5, wherein said fatty acid derivative is selected from the group consisting of free fatty acid, fatty acid chloride, fatty acid alkyl ester, fatty acid vinyl ester and fatty acid ahydride.

7. A process according to claim 1, wherein the phospholipase enzyme is optionally immobilized on an insoluble matrix and is optionally surfactant-coated.

8. A process according to claim 1, wherein said phospholipase enzyme is immobilized on an insoluble matrix and is optionally surfactant-coated.

9. A process according to claim 8, wherein said immobilized phospholipase is surfactant-coated.

10. A process according to claim 1, wherein the phospholipase enzyme that catalyzes the acylation at both the sn-1 and sn-2 positions of said glycerophospholipid is derived from the genus *Aspergillus*.

11. A process according to claim 10, wherein said *Aepergillus* is SANK 11870.

12. A process according to claim 1, wherein the conversion yield of said gylcerophospholipid to 1,2-diacyl-glycerophospholipid is at least 20%.

13. A process according to claim 1, wherein said glycerophospholipid is glycerophosphatidylcholine (GPC).

14. A process for the production of 1,2-diacylated-glycerophospholipids, and their synthetic or natural analogues, in which the 1-and 2-acyl groups are identical and are predetermined, comprising contacting in a microaqueous environment a glycerophospholipid with a carboxylic acid acyl donor, preferably a fatty acid derivative capable of providing the same desired acyl group in the presence of a phospholipase enzyme capable of catalyzing an acylation at both the sn-1 and sn-2 positions of said glycerophospholipid.

15. A process according to claim 1, wherein 1-monoacyl-2-lyso-glycerophospholipid is formed when a solvent, preferably an organic solvent is used.

16. A process according to claim 15, wherein said solvent is tert.-butanol.

17. A process according to claim 1, wherein the product is any one of 1,2-di-acyl-glycerophosphatidylcholine and analoque thereof.

18. A process according to claim 17, wherein the product is 1,2-dilauroyl-glycerophosphatidylcholine.

19. A process according to claim 17, wherein the product is 1,2-di-myristioyl-glycerophosphatidylcholine.

20. A process according to claim 17, wherein the product is 1,2-dipalmitioyl-glycerophosphatidylcholine.

21. A process according to claim 18, wherein the glycerophospholipid is glycerophosphatidylcholine and the acyl donor is vinyl laurate.

22. A process according to claim 19, wherein the glycerophospholipid is glycerophosphatidylcholine arid the acyl donor is vinyl myristate.

23. A process according to claim 19, wherein the glycerohospholipid is glycerophosphatidylcholine and the acyl donor is vinyl palmitate.

24. A process according to any of claim 7, wherein said optionally surfactant-coated phospholipase, capable of catalyzing acylation at sn-1 and sn-2 positions, is physically, ionically or covalently bound to said insoluble matrix.

25. A process according to claim 24 wherein said insoluble matrix is selected from the group consisting of adsorbents, ion-exchange resins and activated insoluble matrices.

26. A process according to claim 24, wherein the insoluble matrix is selected from the group consisting of Dowex® 22, Dowex® 1×2-40, Dowex, 2×8-100, cellulose phosphate, Amberlite® IRA-95, Amberlite® IRA-200 Amberlite® IRA-900, Amberlite® XAD-7, Amberlite® XAD-16, Diannon® SA-10A, Ectoela® cellulose, Sephadex® and sulfoxyethylcellulose, Celite, alumina, silica gel, calcium carbonate, aluminum stearate, charcoal and calcium sulfate.

27. A process according to claim 7, wherein said surfactant is selected from the group consisting of sugar fatty acid esters, sugar alkyl esters, polyol fatty acid esters and polyol alkyl ethers.

28. A process according to claim 25, wherein the surfactant is sorbitan monolaurate, sorbitan monomyristate, sorbitan monopalmitate and sorbitan monostearate.

29. 1-Stearoyl-2-lyso-glycerophospholipids prepared by the process of claim 15.

30. A process for the production of 1-acylated-2-lyso-glycerophospholipids and their synthetic or natural analogues, wherein the 1-acyl group is predetermined, comprising contacting in a microaqueous environment a glycerophospholipid with a carboxylic acid acyl donor in the presence of a phospholipase capable of catalyzing an acylation at the sn-1 position (site) of said glycerophospholipid, in the presence of an organic solvent.

31. A process according to claim 30, wherein the water content in the reaction mixture is less than 30% by volume of the volume of the reaction mixture, preferably less than 5%, more preferably 0.5–3%.

32. A process according to claim 30, wherein said carboxylic acid acyl donor is a fatty acid acyl donor.

33. A process according to claim 32 wherein said fatty acid acyl donor is a saturated or unsaturated, short-, medium- or long-chained linear or branched fatty acid derivative.

34. A process according to claim 33, wherein said fatty acid derivative is selected from the group consisting of free fatty acid, fatty acid chloride, fatty acid alkyl ester, fatty acid vinyl ester and fatty acid anhydride.

35. A process according to claim 30, wherein the phospholipase is phospholipase $A_1$ optionally immobilized on an insoluble matrix and is optionally surfactant-coated.

36. A process according to claim 30, wherein said phospholipase enzyme is immobilized on an insoluble matrix and is optionally surfactant-coated.

37. A process according to claim 30, wherein said immobilized phospholipase is surfactant-coated.

* * * * *